US005656298A

United States Patent [19]
Kitchell et al.

[11] Patent Number: 5,656,298
[45] Date of Patent: Aug. 12, 1997

[54] IMMUNOBOOSTER FOR DELAYED RELEASE OF IMMUNOGEN

[75] Inventors: Judith P. Kitchell, Newton; Stephen C. Crooker, Framingham, both of Mass.

[73] Assignee: DynaGen, Inc., Cambridge, Mass.

[21] Appl. No.: 396,363

[22] Filed: Feb. 28, 1995

Related U.S. Application Data

[63] Continuation of Ser. No. 951,460, Sep. 25, 1992, abandoned.

[51] Int. Cl.$^6$ .................................................. A61K 9/14
[52] U.S. Cl. .................. 424/486; 424/488; 424/489; 424/469
[58] Field of Search ........................ 424/486, 488, 424/489, 469

[56] References Cited

U.S. PATENT DOCUMENTS

| | | | |
|---|---|---|---|
| 3,437,728 | 4/1969 | Renwanz et al. | 424/21 |
| 3,599,150 | 8/1971 | Fetaberg et al. | 424/88 |
| 3,743,720 | 7/1973 | Fosker et al. | 424/88 |
| 4,242,328 | 12/1980 | Hem et al. | 424/157 |
| 4,756,907 | 7/1988 | Beck et al. | 424/85 |
| 4,784,948 | 11/1988 | Scott et al. | 435/68 |
| 4,808,404 | 2/1989 | Bhogal | 424/88 |
| 4,874,613 | 10/1989 | Hsiao | 424/458 |
| 4,897,268 | 1/1990 | Tice et al. | 424/422 |
| 4,919,929 | 4/1990 | Beck | 424/88 |
| 4,921,757 | 5/1990 | Wheatley et al. | 428/402.2 |
| 4,933,185 | 6/1990 | Wheatley et al. | 424/461 |
| 5,008,114 | 4/1991 | Lovrecich | 424/484 |
| 5,008,116 | 4/1991 | Cahn | 424/491 |
| 5,026,538 | 6/1991 | Lieberman et al. | 424/1.1 |
| 5,151,273 | 9/1992 | Korsatko-Wabnegg et al. | 424/465 |

FOREIGN PATENT DOCUMENTS

| | | |
|---|---|---|
| 0266119 | 5/1988 | European Pat. Off. |
| 1237076 | 5/1988 | European Pat. Off. |
| 0333523 | 9/1989 | European Pat. Off. |
| 862376 | 3/1961 | United Kingdom |
| 981242 | 10/1961 | United Kingdom |

OTHER PUBLICATIONS

Esparza I. et al., "Parameters Affecting the Immunogenicity of Microencapsulated Tetanus Toxoid", Vaccine, vol. 10, No. 10, (1992) pp. 714–720.

J. Freund, "The Effect of Paraffin Oil and Mycobacteria on Antibody Formation and Sensitization", Amer. Journal Clinical Pathology, 21(7), (1951) pp. 645–656.

M.R. Hilleman, "Immunologic, Chemotherapeutic and Interferon Approaches to Control of Viral Disease", American Journal of Medicine, vol. 38, (1965) pp. 751–766.

R. Langer et al., "Polymers for the sustained release of proteins and other macromolecules", Nature, vol. 263, (1976) pp. 797–800.

I. Preis eta l., "A Single–Step Immunization by Sustained Antigen Release", Journal of Immunological Methods, 28 (1979) pp. 193–197.

J. Kohn et al., "Single–step immunization using a controlled release, biodegradable polymer with sustained adjuvant activity", Journal of Immunological Methods, 95 (1986) pp. 31–38.

*Primary Examiner*—Raj Bawa
*Attorney, Agent, or Firm*—Wolf, Greenfield & Sacks, P.C.

[57] ABSTRACT

An immunobooster capable of delivering an immunogen to an individual or animal in a controlled release manner is described. The immunobooster contains an immunogen/hydrophobic polymer matrix with a swelling agent such that the swelling agent can swell in an aqueous environment and burst the matrix. The immunogen is released in a pulsed release manner after a desired time interval has elapsed subsequent to administration of the immunobooster. The immunobooster eliminates the need for multiple administrations of immunogen in order to build lasting immunity. Also described are methods of preparing and using the immunobooster, and kits containing the immunobooster.

48 Claims, 7 Drawing Sheets

FIG. 5

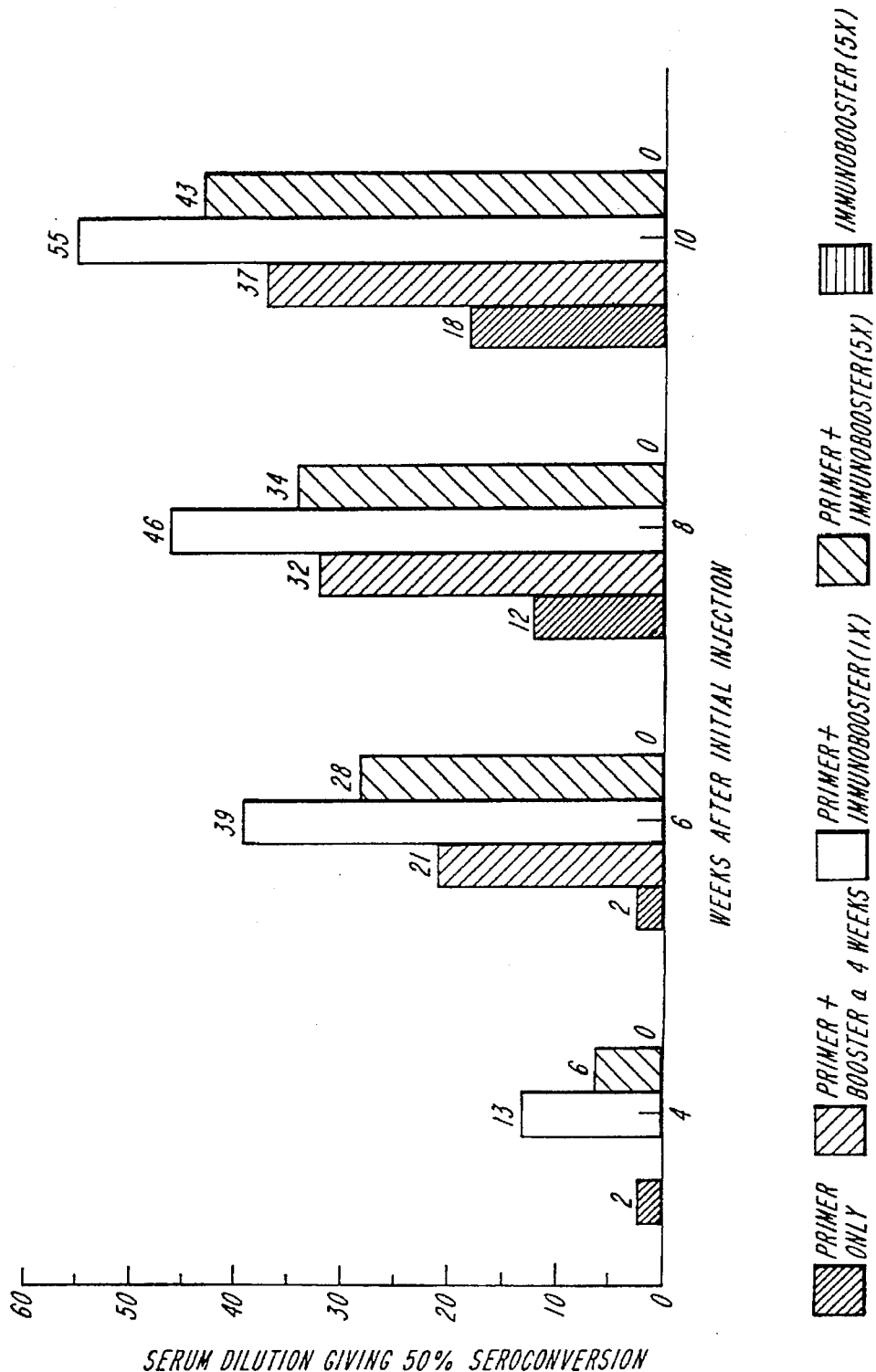

IMMUNOBOOSTER FOR DELAYED RELEASE OF IMMUNOGEN

This application is a continuation of application Ser. No. 07/951,460, filed Sep. 25, 1992, now abandoned.

BACKGROUND

Some immunological reagents can protect persons and animals from many microbial and viral infections, from toxic incapacitation or death, and from certain noninfectious diseases. In some cases, post-onset treatment of these conditions is possible with these reagents. These immunological reagents are effective only when a proper administration regimen is followed. The proper method of administration often includes multiple sequential exposures to the immunogenic material over a period of weeks or months in order to stimulate an immunological defense. For example, in a classic immunization regimen, a single dose of vaccine, a "primer" is delivered in one injectable or oral dose, producing a short-term immunity. Vaccination is repeated one or more times, with "booster" doses, producing a secondary immune response which gives rise to a long-lasting immunity. The availability of trained medical or veterinary personnel and careful medical record maintenance are required to implement these multiple administrations. Moreover, such multiple administrations may not be logistically feasible for certain groups of people, such as in areas where the population is dispersed, as well as for certain livestock, such as chickens and cattle, where the number of individual animals to be dosed is very large.

Several different approaches have been tried to solve this problem. One approach is to prolong the presence of immunogen in the individual or animal from a single administration, thereby reducing the need for subsequent doses of the immunogen. For injectable vaccines, the length of time that vaccine immunogen is present as a result of one injection can be extended by utilizing an oil based medium such as Freunds' Complete Adjuvant, which degrades and releases antigen slowly. (Freund, J., Am. J. Clin. Pathol. 21:645 (1951)). Because of the degradation products produced, however, this medium is not approved for use in humans. Various synthetic polymers have been used as binders in delivery systems which are capable of sustained release of proteins for prolonged periods. (Langer, R. and Folkman, J., Nature 263:797 (1976); Langer, R. and Preis, I., J. Immunol. Methods 28:193 (1979)). Many of these synthetic polymers, however, are not biodegradable, and thus also have limited use in humans. Other polymers which are biodegradable or bioerodible have been developed as well. (Tice and Gilley, U.S. Pat. No. 4,897,268; Beck, U.S. Pat. No. 4,919,929; Kohn, J., Niemi, S. M., Albert, E. L., Murphy, J. C., Langer, R. and Fox, J. G., J. Immunol. Methods 95:31–38 (1986)). These polymers, however, result in gradual and continuous release of antigen, rather than delayed release, and thus do not provide for the most effective immunization.

Controlled release delivery systems whose object is to produce delayed release of immunogen, have also been described. Wheatly, Langer and Eisen were awarded a patent which involves entrapping the substance to be delivered in liposomes and encapsulating the liposomes in a polymer matrix. The liposomes are either sensitive to specific stimuli such as temperature, pH, or light, or the liposomes contain an enzyme in the matrix which produces delayed release of the substance from the matrix encapsulated liposomes. (U.S. Pat. No. 4,921,757). Such a system is complex. Moreover, the pulsing depends on the integrity of the enzymatic activity. These inventors also describe a system involving formation of ionically-coated microcapsules around the substance to be delivered with a microcapsule core-degrading enzyme, resulting in delayed release of the substance. (U.S. Pat. No. 4,933,185). The above described delivery systems require an encapsulation step wherein the immunogen is encapsulated in a liposome or microcapsule. All such systems which require a shell around an active ingredient suffer from the inherent problem that a flaw in the shell can result in a drastically changed pattern of release.

Beck, Flowers, Cowsar and Tanquary describe antigen containing microparticles for immunization of female reproductive organs designed to produce delayed release of antigen by encapsulating a core of antigen with a shell matrix material. (U.S. Pat. No. 4,756,907). This system is designed to release the antigen, after transport of the microparticles, by disruption of the outer shell of the microparticles by some endogenous factor, e.g., the difference in pH of the mucosal fluids in the vagina as compared to the pH of the cervix and uterus. Such a system can only be utilized in a limited number of situations. There is considerable variation among individuals which restricts the use of such a system. This system also suffers from problems associated with shells. The Beck patent also describes intermittent release of antigen produced by multi-layering degradable polymer and antigen. This system requires the manufacture of a multi-layered device. The manufacturing of such a product is complex, requiring multiple production steps.

SUMMARY OF THE INVENTION

There is a need for an immunobooster capable of following a single dose to simulate the release profile of the multiple doses required for long lasting immunity. The immunobooster of the present invention does not require encapsulation of the immunogen to achieve the desired result of controlled release of the immunogen. Rather, the immunogen is placed in a hydrophobic polymer matrix along with a swelling agent. It is the characteristics of the polymer, the special characteristics of the swelling agent, and the relationship of the two materials in a matrix format that delays the release of the immunogen for specified periods of time after it is administered.

The present invention provides an immunobooster for delivering immunogen to an individual or animal. The immunobooster contains an immunogen/hydrophobic polymer matrix with a swelling agent for bursting the matrix such that delivery of the immunogen occurs in a controlled release manner. Preferably, the swelling agent is retained by the matrix for a prolonged period of time until a certain degree of swelling has occurred, at which point the swelling bursts the immunogen polymer matrix resulting in delayed release.

The present invention also pertains to an immunobooster for delivering immunogen to an individual or animal that contains at least two separate immunogen formulations. Preferably, one of the formulations contains free immunogen which mimics the immunogen component of classical primer vaccines in which only a single dose of immunogen is included. Preferably, the other immunogen formulation is a combination of immunogen and swelling agent distributed in a hydrophobic polymer matrix, such that the immunogen is released upon bursting of the matrix by the swelling agent after a period of time.

The present invention also pertains to a method for immunizing an individual or animal by administering an immunogen/hydrophobic polymer matrix containing a swelling agent. The swelling agent is capable of bursting the matrix after a period of time, thereby releasing the immunogen in a controlled release manner. Preferably, free immunogen will be co-administered with the immunogen/ swelling agent/polymer matrix as part or, the immunobooster system.

The present invention also pertains to a method for preparing a hydrophobic polymer matrix containing a swelling agent and an adjuvant. This matrix may contain an immunogen as well. It is permitted, however, to provide the immunogen and adjuvant in separate matrices.

The present invention also pertains to a method for preparing a hydrophobic polymer matrix containing a swelling agent capable of bursting the matrix. Preferably, this method produces the polymer matrix in the form of rods or powders.

The present invention also pertains to a method for preparing a polymer matrix which is capable of bursting after a prolonged period of time. The method includes combining an effective amount of a swelling agent with a polymer so as to form a swelling agent/polymer matrix, and then shaping the swelling agent/polymer matrix into forms capable of being administered to an individual or animal. Preferably, at least one immunogen is included in the matrix.

The present invention further pertains to kits useful in delivering immunogen to an individual or animal in a controlled release manner. The kit includes a packaged immunogen/polymer matrix with a swelling agent for bursting the matrix. The kit also contains a liquid suspending vehicle for the matrix and instructions providing information to the user regarding the use of the immunogen/swelling agent/polymer matrix for delivering immunogen in a controlled release manner. Preferably, the kit also contains a package of free immunogen.

It is an object of the invention to provide effective protection to an individual or an animal from microbial, viral or toxic incapacitation or death.

It is another object of the invention to provide effective immunological treatment of infectious and noninfectious diseases and treatment for exposure to toxic substances.

It is another object of the invention to achieve long-lasting immunity to microbial, vital or toxic incapacitation or death.

It is yet another object of the invention to eliminate the need for multiple administrations of immunogen to achieve long-lasting immunity.

It is yet another object of the invention to deliver primer and booster doses of an immunization regimen in a single administration to an individual or animal.

It is yet a further object of the invention to deliver an immunogen to an individual or animal in a controlled release manner.

Still another object of the invention is to administer an immunogen to an individual or animal in a pulsed release manner, such that there is a prolonged period of time between the time of the initial administration of an immunogen-containing formulation and release of the immunogen into the individual or animal.

BRIEF DESCRIPTION OF THE DRAWINGS

Figure 5:
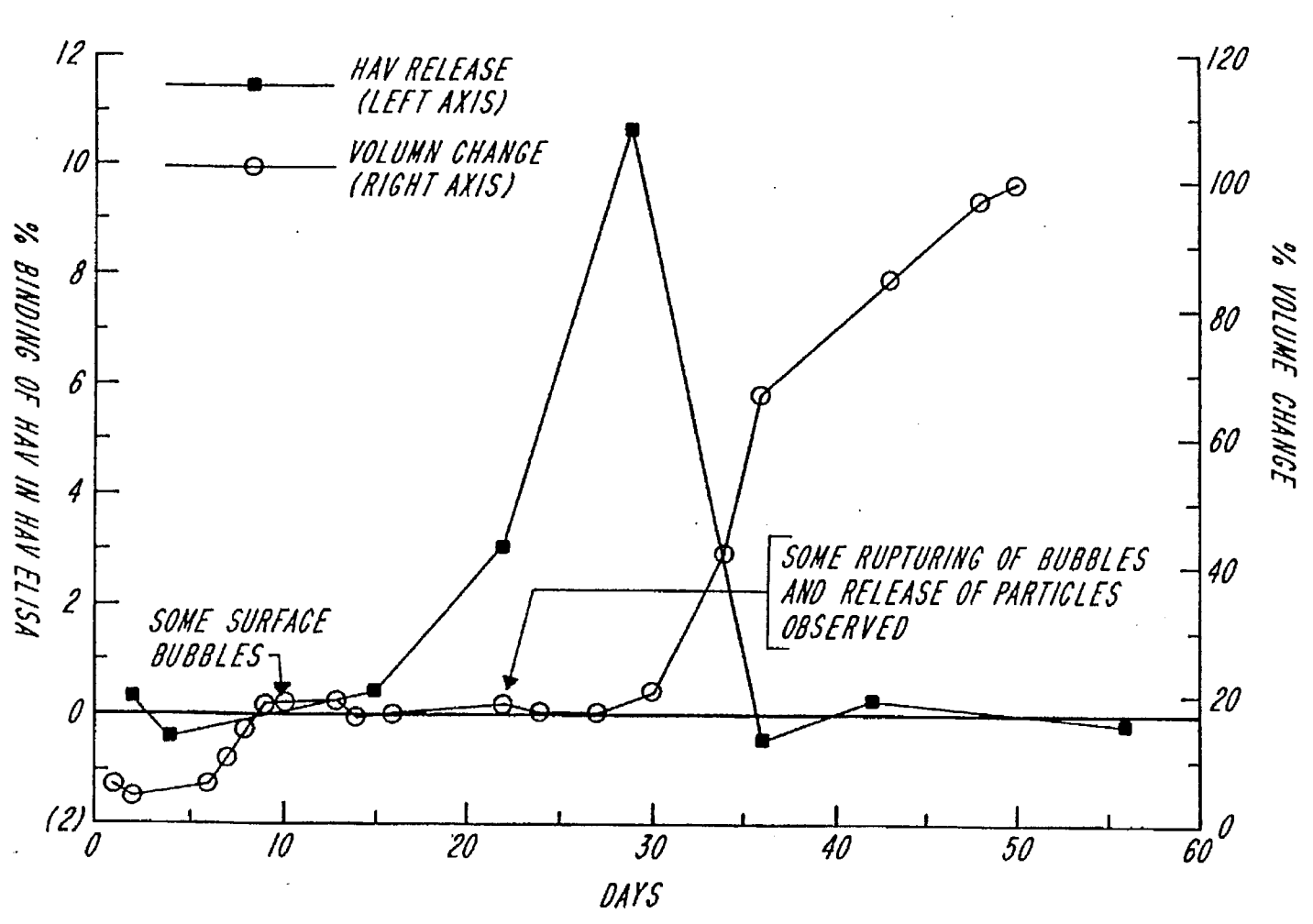

FIG. 5 depicts in vitro swelling and release of immunogen (Hepatitis A Vaccine), as measured by the percent of HAV binding in an ELISA assay from dried aluminum hydroxide gel/PLGA/Hepatitis A Vaccine rods as a function of time.

FIG. 7 depicts the in vivo activity of immunobooster when given along with a primer dose of aluminum hydroxide gel-Hepatitis A Vaccine as measured by the serum level of anti-HAY antibody (seroconversion) in mice. Also shown is the lack of activity when the immunobooster is given without primer.

DETAILED DESCRIPTION

Figure 1:
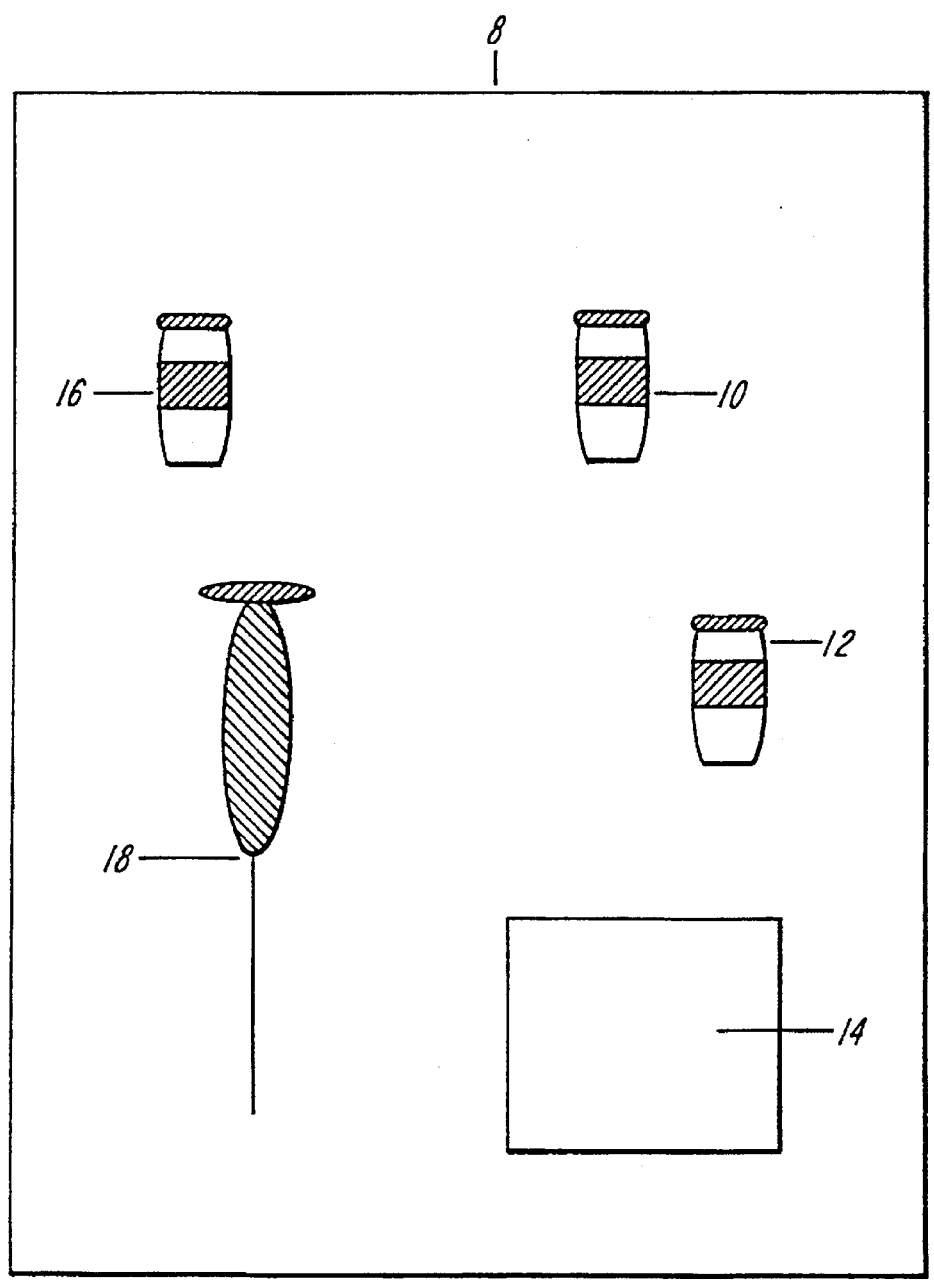
FIG. 1 depicts a kit including a package containing an immunogen/polymer matrix with a swelling agent, free immunogen, suspending vehicle, syringe and instructions.

The present invention pertains to an immunobooster for delivering an immunogen to a subject. The immunobooster includes an immunogen/hydrophobic polymer matrix containing a swelling agent which is capable of causing a delayed bursting of the matrix. The immunobooster is constructed and arranged to deliver the immunogen to the subject in a controlled release manner.

The term immunobooster means at least one immunogen formulation which can produce a secondary immune response. The immunobooster may also include an immunogen formulation which produces a primary immune response. A primary immune response produces a short-term immunity, and results from initial exposure to an immunogen. A secondary immune response produces a long-lasting immunity, and results from multiple exposure to the same immunogen. For immunoboosters containing an immunogen formulation only for producing the secondary immune response, a different immunogen formulation for producing the primary response can be administered physically independently of, or in conjunction with, the immunobooster of the invention. Preferably if two separate formulations are co-administered, then they are administered at about the same time. In the preferred embodiment, the immunobooster includes both an immunogen formulation from which immunogen is released at the time of administration, producing the primary immune response, and a second immunogen formulation which releases immunogen after a period of time subsequent to administration of the immunobooster, thus producing the secondary immune response. This second immunogen formulation is an immunogen/swelling agent/ polymer matrix which is designed to burst after a period of time, releasing the immunogen. Depending upon at least the immunity required and the immunogen used, the immunobooster may contain one or it may contain multiple controlled release immunogen formulations which release immunogens at different times subsequent to administration of the immunobooster.

The delayed release of immunogen from the immunobooster is a function of the type and amount of a swelling agent in the immunogen/polymer matrix and of the exact polymer utilized. The matrix at first is able to retain the swelling agent and immunogen, but after a delay, the swelling agent bursts the matrix, releasing the immunogen into the subject. The term controlled release of immunogen is intended to include release of immunogen from the immunobooster such that total release does not occur immediately upon administration of the immunobooster.

The term pulsed release of immunogen is intended to include release of immunogen after administration of the immunobooster such that release occurs in a discrete burst after a prolonged period of time subsequent to the administration. In some circumstances, there might be a low level of release upon administration which continues for some period of time until a burst releasing a high level of immunogen occurs.

The term prolonged period of time is intended to encompass a period of time sufficient to permit the desired secondary immunologic response to the release of the immunogen from the immunogen/polymer matrix. This period varies depending upon at least such factors as the particular immunogen used, the amount of immunogen used in the immunobooster, the amount of immunogen used originally to elicit the primary immune response, and the type of species being immunized. Typical time periods would be 3 weeks, 6 weeks, 3 months, 6 months, and 12 months.

For example, certain currently accepted immunization regimens include the following. For Hepatitis B Vaccine (RECOMBIVAX HB), the recommended administration times are a first dose at elected date; a second dose at 1 month after first dose; and a third dose at 5 months after second dose. See Product Information, Physician's Desk Reference, Merck Sharp & Dohme (1990), at 1442–43. For Diptheria, Tetanus and Pertussis vaccines (Diptheria and Tetanus Toxoids and Pertussis Vaccine Absorbed USP), the recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, Physician's Desk Reference, Merck Sharp & Dohme (1990), at 879. Desired time intervals for delivery of multiple doses of a particular immunogen can be determined by one of ordinary skill in the art employing no more than routine experimentation. Once the desired time intervals for delivery are determined, an appropriate amount of swelling agent, an appropriate degree of hydration of the swelling agent, and an appropriate polymer are chosen for the immunobooster, such as to cause the immunogen/polymer matrix to burst at the desired time interval.

The term immunogen is intended to include any substance which is capable, under appropriate conditions, of inducing the formation of antibodies and/or inducing cellular immunity. The formation of antibodies depends on at least such factors as introduction of the immunogen into an appropriate species, on the quantity of immunogen introduced, and on the route and frequency of introduction. Immunogens include proteins, polysaccharides, nucleoproteins, lipoproteins, polypeptides, and small molecules suitably linked to proteins, polypeptides or other carrier molecules. Examples of immunogens are inactivated hepatitis A virus, polio virus, inactivated feline leukemia virus, and malarial vectors, e.g., sporocite surface peptides.

The term free immunogen is intended to mean immunogen that is in a form that is available substantially upon administration for inducing a primary immune response. Such forms have been in use for many years and are well known to those of ordinary skill in the art. It includes immunogen that is not incorporated in a matrix such as a polymer matrix. The free immunogen may or may not be bound to an adjuvant (a material which enhances the cellular response to immunogens). The free immunogen is delivered to the subject, acting as the equivalent of a "primer" dose in a classic multiple administration immunization regimen. In such a configuration, the immunobooster would also contain at least a second immunogen formulation as part of the immunogen/polymer matrix for delivery of a "booster" dose after a period of time. The immunogen/swelling agent/ polymer matrix may include immunogen adsorbed to a colloidal adjuvant such as aluminum hydroxide gel or immunogen covalently bonded to an adjuvant. The adjuvant also may be a separate component in the matrix along with the immunogen. Still further, adjuvant may be present in a separate polymer/swelling agent matrix. In the embodiment where the immunogen is combined with the adjuvant, it may be combined prior to incorporation in the polymer matrix, forming an immunogen-adjuvant complex. The immunogen-adjuvant complex may be distributed in a homogeneous fashion throughout the matrix. The term complexed immunogen is intended to include immunogen that is covalently linked or adsorbed onto the adjuvant.

The term polymer is intended to include molecules composed of monomers which do not have significant adverse physiological effects when administered in vivo. A polymer made from more than one kind of monomer is called a copolymer. Polymers may be natural or synthetic. The polymers useful in the invention are hydrophobic. By hydrophobic it is meant that the formed polymer matrix, absent a swelling agent, would not attract water and swell very much in an aqueous environment.

Preferably the polymer is biodegradable. A biodegradable polymer means polymers capable of degrading in vivo. Examples of biodegradable polymers which may be used in this invention include poly (lactic/glycolic) acid copolymers (PLGA), polylactic acid (PLA), polyglycolic acid (PGA), polyesters, e.g., polyorthoesters, polylactones, polyanhydrides and polyaminoacids. Polymers prepared from glycolida and lactide dimers, e.g., PLGA, PLA and PGA, are known to undergo slow hydrolysis when implanted in tissue; the by-products of their hydrolysis (lactic and glycolic acids) are normal metabolites. Such polymers are generally believed to be non-toxic, are relatively non-inflammatory, and are non-tissue reactive. These polymers also exhibit moderate tensile and compressive strength and pliability. Poly (L lactic) acid is the optically active form of the lactic acid polymer. Poly DL lactic acid is an optically inactive form of the polymer. The preferred biodegradable polymer is PLGA. PLGA copolymers can be composed in either poly (DL-lactic/glycolic) acid or poly(L-lactic/glycolic) acid forms.

The specific lactide/glycolide ratio of the PLGA polymer and the molecular weight (size) distribution of the polymer are factors considered when designing the immunobooster. The choice of which PLGA to use is determined by the desired release duration for the immunogen. The preferred polymers are in the range of about 95:5 D,L lactide/glycolide to about 40:60 D,L lactide/glycolide, most preferably about 50:50. The preferred polymers have weight average molecular weights ($M_w$) in the range of about 40,000 to about 300,000 daltons, most preferably about 50,000 daltons. The preferred polydispersity ($M_w/M_n$) is about 2.

The term matrix is intended to include a composite of polymer and one or more other components which are distributed in a homogeneous fashion throughout the matrix. The polymer and components are compressed so that the polymer closely conforms to the components if the components are particulate, or so that one or more components are dissolved in the polymer. The components may include immunogen-adjuvant complex, immunogen, swelling agent and adjuvant. The matrix is made of a material capable of being shaped into various forms, e.g., a nanoparticle, a microparticle or a monolithic rod, sphere or other shape. The preferred form for the matrix is a rod or powder. A method for the preparation of such rods and powder is described in Example 1.

The term immunogen/polymer matrix is intended to include a matrix of polymer and immunogen. Such a matrix may also include other components, e.g., a swelling agent. Preferably, the immunogen is complexed with an adjuvant prior to incorporation in the polymer matrix. Alternatively, the immunogen is not complexed to adjuvant in the immunogen/polymer matrix. In an immunobooster which contains non-complexed immunogen as part of an immunogen/polymer matrix, the matrix may also contain adjuvant or the immunobooster may contain a separate formulation which releases adjuvant at the same time as the immunogen is released.

The term non-aqueous immunogen/polymer matrix is intended to include any immunogen/polymer matrix that is substantially free of water. Preferably it contains no water. Some water may be present as long as the amount of water does not impede or detrimentally affect the desired timing of release of immunogen from the matrix.

The term swelling agent is intended to include any substance which exhibits biphasic swelling characteristics in an aqueous environment (i.e. a slow swelling phase followed by a rapid swelling phase), such that if it is part of an immunogen/polymer matrix, it can, upon reaching a rapid swelling phase, burst the matrix after a prolonged period of time subsequent to administration of the matrix into a subject. Typical time periods of delay would be 2 weeks to 6 months. The preferred swelling agent, when dispersed in an immunogen/polymer matrix, initially effects changes in the volume of the matrix very slowly, resulting in retention of the immunogen in the matrix. After a period of time, the swelling agent swells the matrix rapidly, allowing the bulk of the immunogen to be released in a pulsed manner. The swelling agent should be sufficiently dry and should be present in sufficient amount in the matrix so that when the matrix is introduced into an aqueous environment, it will swell sufficiently to burst the matrix used in the immunobooster. The preferred swelling agent is also an adjuvant.

The term non-aqueous swelling agent formulation is intended to include a swelling agent formulation containing preferably no water. Some water may be present as long as the amount of water does not detrimentally affect the swelling agent's intended function of bursting the matrix.

The preferred swelling agents of this invention swell very slowly in water. For example, the preferred range for equilibration for a mixture of water and dried aluminum hydroxide gel to form a 1% gel is one week to four weeks. Examples of swelling agents are: aluminum hydroxide; aluminum phosphate; calcium phosphate; lanthanum, cerium, and cadmium salts; and bentonite (colloidal hydrated aluminum silicate). The preferred swelling agent is dried aluminum hydroxide gel. The dried gel is also known as aluminum hydroxide hydrate ($Al_2O_3 \cdot XH_2O$ or $AL(OH)_3 \cdot XH_2O$). Liquid slurry forms of aluminum hydroxide gel (also known as alumina gel) are well-known adjuvants and are often referred to as Alum or Alum gel by immunologists. (Alhydrogel is a trade name for liquid aluminum hydroxide gel.)

An effective amount of the swelling agent is used in the immunogen/polymer matrix. An effective amount of swelling agent is that amount capable of bursting in an aqueous environment the immunogen/polymer matrix after a prolonged period of time so as to release the immunogen. To a certain extent, as described in Example 3, increasing the amount of swelling agent delays the onset of rapid swelling. An effective amount can be determined by considering at least the swelling agent used, the polymer used, the particular size and geometry of the shaped polymer matrix, and the time period desired to elapse before the swelling agent bursts the polymer matrix. An effective amount can be determined by one of ordinary skill in the art employing such factors using no more than routine experimentation. For example, a PLGA polymer matrix designed to release immunogen from the matrix in about two to six weeks subsequent to administration into a subject might contain 10% dried aluminum hydroxide gel incorporated into 50:50 D,L lactide/glycolide. Example 1 describes the preparation of dried aluminum hydroxide gel/PLGA rods and powder.

Means for preparing the immunobooster include the mixing of dry immunogen plus dry adjuvant, or addition of dry adjuvant-immunogen complex, swelling agent and polymer. If the adjuvant, the adjuvant-immunogen complex, or the swelling agent are suspensions or solutions in buffer, it is preferable to remove the buffer prior to incorporation in the polymer.

In the preferred embodiment where dried aluminum hydroxide gel is the swelling agent, this gel is also released with immunogen absorbed on similar gel, or co-resident non-complexed immunogen from the immunogen/polymer matrix upon bursting of the matrix. Preferably, the released aluminum hydroxide gel also acts as an adjuvant. Alternatively, other adjuvants may be incorporated into the immunogen/polymer matrix, either complexed with immunogen or as a separate component, which upon bursting of the matrix are released along with immunogen, or a separate formulation may be delivered.

The term adjuvant is intended to include any substance which is incorporated into or administered simultaneously with the immunogen which potentiates the immune response in the subject. Adjuvants include aluminum compounds, e.g., gels, aluminum hydroxide and aluminum phosphate gels, and Freund's complete or incomplete adjuvant (in which the immunogen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), leutinan, pertussis toxin, lipid A, saponins and peptides, e.g., muramyl dipeptide. Rare earth salts, e.g., of lanthanum and cerium, may also be used as adjuvants. The preferred adjuvant is dried aluminum hydroxide gel. The amount of adjuvant required depends upon the subject and the particular adjuvant and immunogen used in the immunobooster and can be readily determined by one skilled in the art without undue experimentation.

Administration of the immunobooster of this invention may be made by any method which allows the immunogen to be delivered to the subject. Typical methods of administration use an immunobooster which can deliver immunogen orally, by injection or by implantation. The preferred method is by injection into the tissues of the subject. Injections include intradermal, subcutaneous, intramuscular and intraperitoneal administration. The immunobooster may be administered as a liquid suspension or as a solid dose. The term subject is intended to include mammals. Preferably the subject is an animal that is commercially used as livestock, a pet, or a human being.

The term effective immunization is intended to include that degree of immunization which protects the individual or animal from an infectious or noninfectious disease, toxic incapacitation or death, or which mitigates the effects of such diseases or exposures. Effective immunization often requires multiple sequential exposure to the immunogen over a period of weeks or months. An effective amount of an immunobooster is that amount which is sufficient to invoke the secondary immune response.

This invention also pertains to a method for immunizing an individual or animal in such a way so that the need for multiple administrations of a particular immunogen is alleviated. Such immunization is accomplished by administering to the individual or animal the immunobooster described above.

This invention further pertains to a method for preparing a polymer matrix including a swelling agent. The method involves combining an effective amount of a swelling agent with a polymer forming a swelling agent/polymer matrix. The method also involves the step of shaping the swelling agent/polymer matrix into forms capable of being administered to a subject. Preferably the swelling agent/polymer matrix also includes an immunogen. The immunogen preferably is incorporated into the matrix, prior to shaping.

The matrix may be prepared by dissolving the polymer in a solvent. The solvent is selected based on its ability to dissolve the polymer. One of ordinary skill in the art would know what solvent to select for a particular polymer based on such factors as polymer solubility, ease of removal, compatibility with the immunogen and toxicity. An example of a solvent useful for dissolving PLGA is methylene chloride. The swelling agent, as defined above, is added to the solution. The suspension of the immunogen, polymer, solvent, adjuvant and swelling agent may be cast on a plate. The casting is dried and extruded or molded into the desired form, e.g., beads or rods which can be further processed into powder by grinding. Preferably, an immunogen is added to the suspension prior to casting. This method is further described in Examples 5 and 7. The method produces rods or powder of a polymer matrix which contain a swelling agent. The preferred polymer is PLGA and the preferred swelling agent is dried aluminum hydroxide gel. Preferably, the dried aluminum hydroxide gel comprises between about 1% and about 40% of the matrix. More preferably it comprises between about 5% and about 20% of the matrix. Most preferably it comprises between about 10% and about 15% of the matrix.

This invention further pertains to kits useful in delivering immunogen to an individual or animal. The kits contain an immunobooster according to the invention, as well as instructions for use. For example, the kit 8, as shown in FIG. 1, may contain at least one packaged immunogen/polymer matrix 10 including a swelling agent with instructions 14 providing information to the user regarding the use of the matrix. A suspending vehicle 12 may be included. There may be multiple packages of immunogen/polymer matrix, corresponding to the number of different immunogen/polymer matrix formulations for which the kit is designed. For example, if multiple pulse releases of immunogen are required for a particular immunization regimen, the number of packages may correspond to that number, with each package containing a different immunogen/polymer matrix with swelling agent, designed to burst after different periods of time subsequent to administration of the immunobooster. Preferably, a package containing free immunogen 16 is also provided in the kit. A syringe 18 may also be provided. The syringe 18 may be preloaded with a particular immunogen/polymer matrix including swelling agent. If free immunogen is provided in the kit, the syringe 18 may also be preloaded with the free immunogen.

The following non-limiting examples further illustrate the present invention.

Example 1

Preparation of Dried Aluminum Hydroxide Gel/ PLGA Matrix Rods

In order to prepare rods and powders of dried aluminum hydroxide gel/PLGA, dried aluminum hydroxide gel was suspended in a polymer solution of PLGA. Dried aluminum hydroxide gel was obtained from Aldrich Chemical Co., Milwaukee, Wis. (Aluminum hydroxide hydrate dried gel, Catalog #23,918 6). The polymer (PLGA) used was DuPont Medisorb 50:50 D,L lactide/glycolide of inherent viscosity~0.8 dl/g. (Obtained from Medisorb Technologies International, L.P. Cincinnatti, Ohio 45242, Medisorb 50:50 DL). An aliquot of 3 g polymer was added to methylene chloride and stirred. The sample was then filtered and dried. The weight of the recovered material was 2.9718 g. To the dry polymer, 30 ml methylene chloride was added. An aliquot of dry aluminum hydroxide gel (from Aldrich), 0.3309 g, was added under nitrogen. The suspension was stirred, then cast under nitrogen on a glass plate and spread with a Boston Bradley blade (gap set at 0.025 inch thickness). The casting was vacuum dried and 2.5385 g was recovered (77% yield). The casting was extruded at 55°–65° C. Pliable rods were obtained.

Example 2

Control of Swelling Rates by Choice of Polymer Composition and Viscosity

Figure 2:
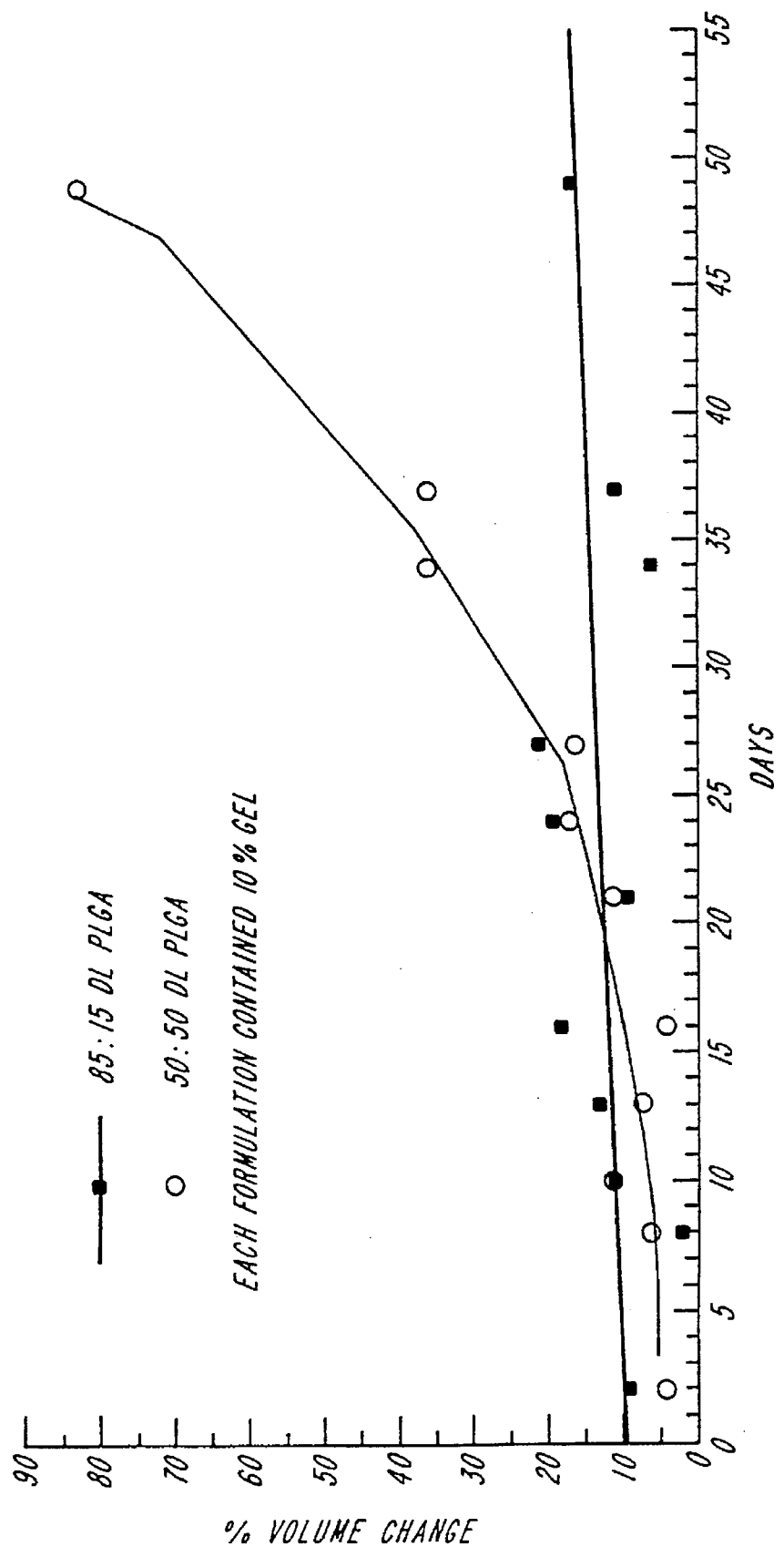
FIG. 2 depicts in vitro swelling of 10% dried aluminum hydroxide gel/PLGA rods of differing polymer substituent ratios as a function of time.

Two polymer/dried aluminum hydroxide gel matrices were prepared as described in Example 1. The polymers used were: 50:50 DL PLGA; and 85:15 DL-lactide/glycolide. Polymer/dried aluminum hydroxide gel castings (10% gel) were prepared as described in Example 1, except that they were not cast under nitrogen. The castings were extruded into rods. The rods were cut into 1 cm lengths and accurately measured. The initial volume of each rod was calculated. The rods were placed in separate vials with phosphate buffered saline and maintained at 37° C. Periodically the rods were remeasured and new volumes were calculated. The rods made with the 50:50 DL PLGA showed biphasic swelling behavior in the period measured (49 days). After remaining at a swelling of about 20% for 4 weeks, the rods swelled rapidly and during weeks 5–7 showed surface bumps, breakage, and release of particles. The rods made with the 85:15 PLGA remained at relatively constant volume (about 20% increase from initial volume) for seven weeks and no bubbles or ruptures appeared. The results are shown in FIG. 2.

Example 3

Swelling of 0–20% Dried Aluminum Hydroxide Gel Rods

Figure 3:
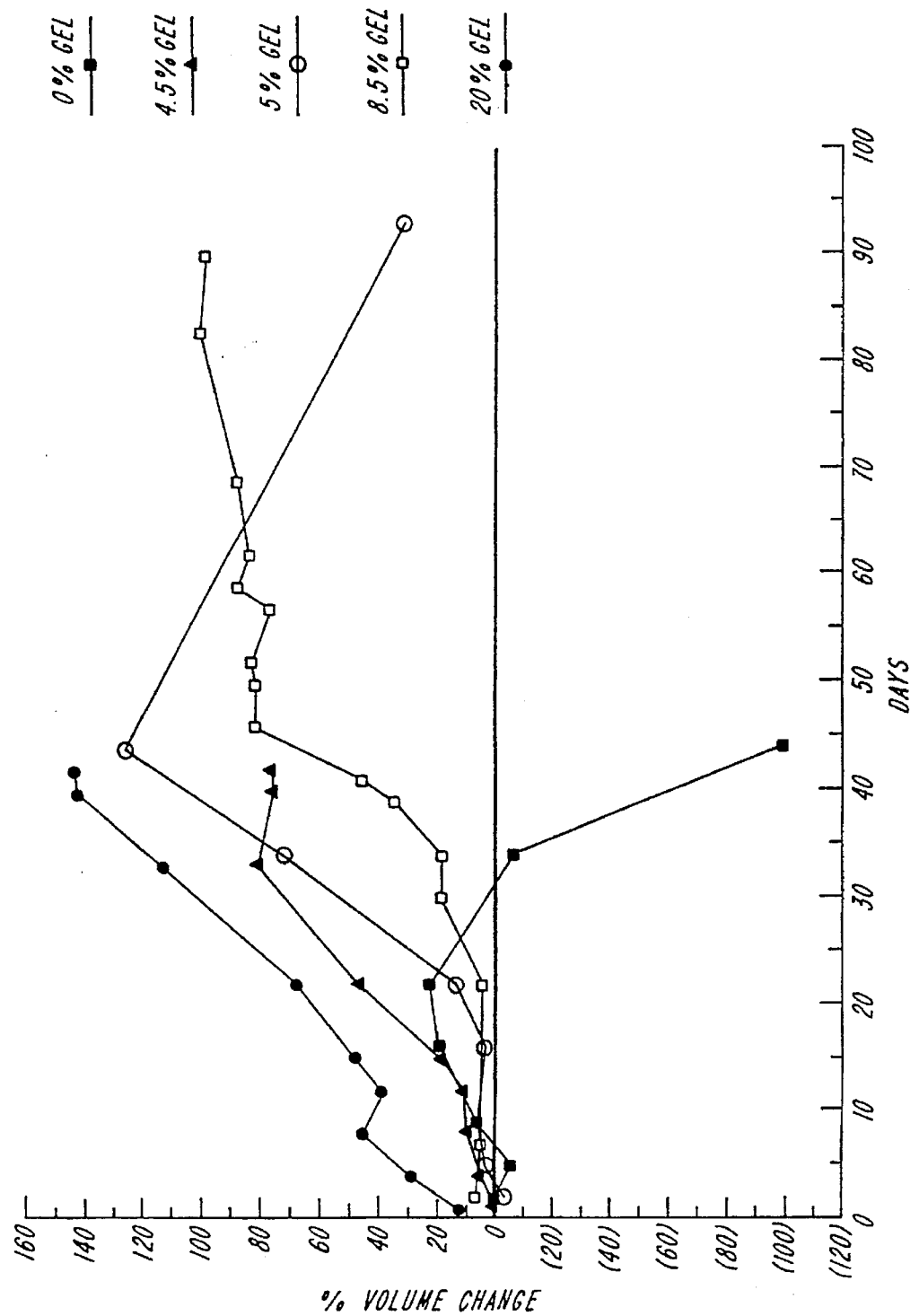
FIG. 3 depicts in vitro swelling of 0–20% dried aluminum hydroxide gel rods as a function of time.
Figure 4:
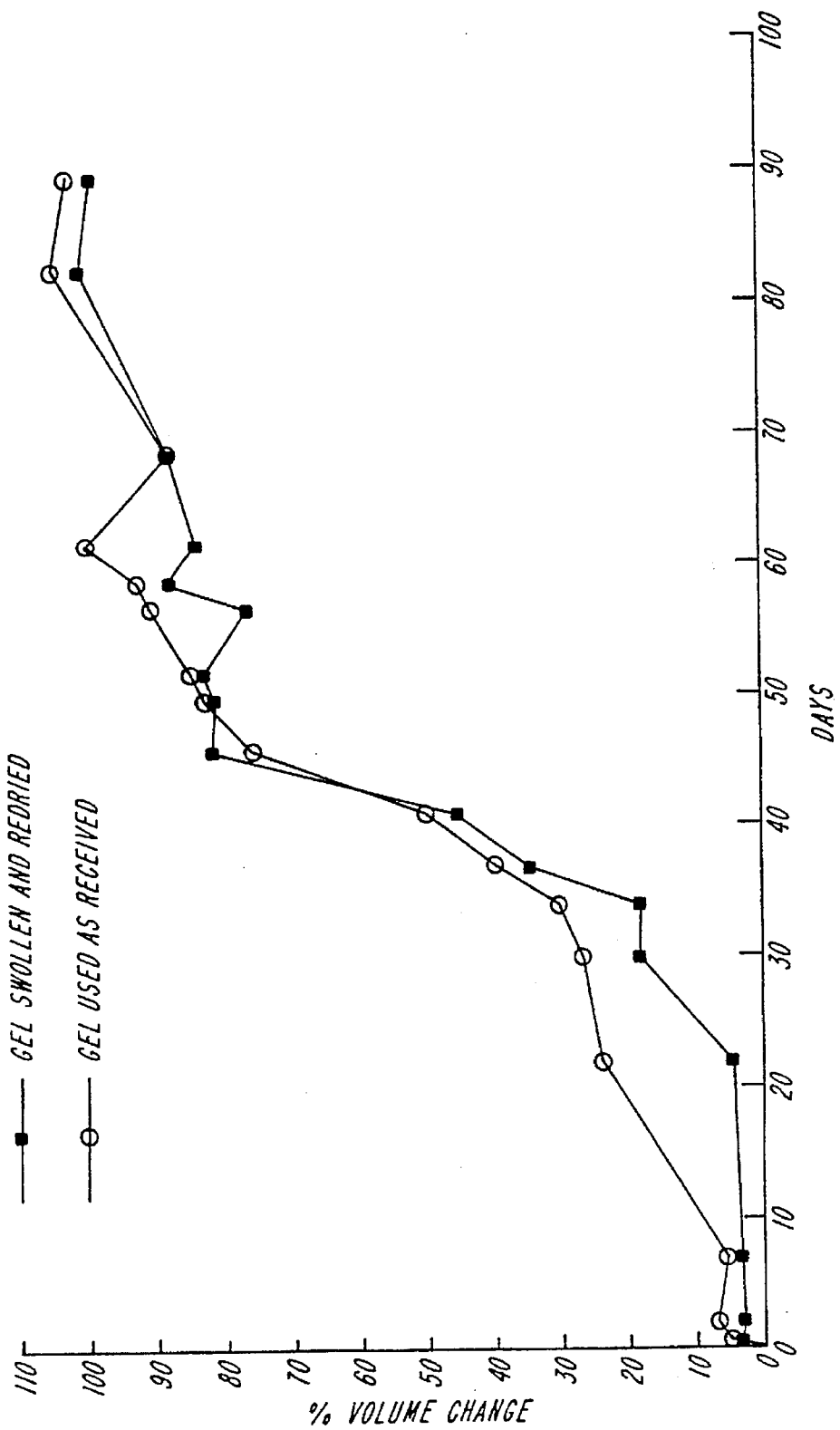
FIG. 4 depicts swelling of 8.5% dried aluminum hydroxide gel rods, prepared either with dried aluminum hydroxide gel as purchased or with swollen and redried aluminum hydroxide gel, as a function of time.
Figure 6:
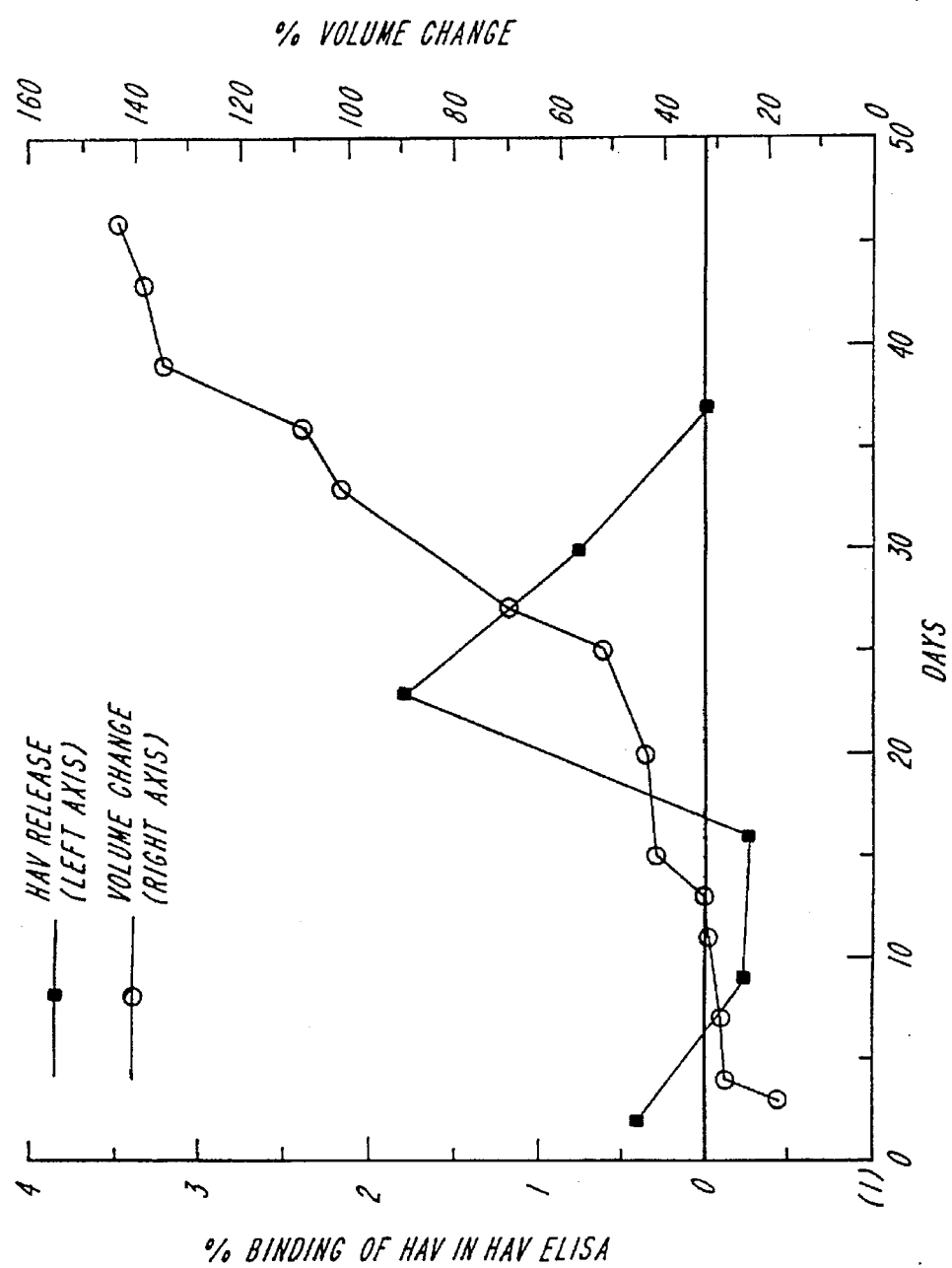
FIG. 6 depicts in vitro swelling and release of aluminum hydroxide gel-bound immunogen (Hepatitis A Vaccine) as measured by the percent of HAV binding in a HAV ELISA assay, from dried aluminum hydroxide gel/PLGA/aluminum hydroxide-Hepatitis A Vaccine rods as a function of time.

Volume changes of PLGA rods differing in dried aluminum hydroxide gel content were measured as a function of time by the procedure described in Example 2. The results are shown in FIG. 3. PLGA rods containing no aluminum hydroxide gel swelled slightly. Increasing amounts of dried aluminum hydroxide gel over the range of 5–8.5% caused increased delays in swelling and very large increases in volume. Matrix containing 20% dried aluminum hydroxide gel swelled much more rapidly, indicating that the limit of loading preferably is between 8.5% and 20% for that matrix system.

Example 4

Swelling of Dried Aluminum Hydroxide Gel/PLGA Rods Prepared With Either Dried Aluminum Hydroxide Gel as Purchased or With Swollen and Redried Aluminum Hydroxide Gel Rods of 8.5% dried aluminum hydroxide gel/PLGA were prepared either with dried aluminum hydroxide gel as purchased or with swollen and redried aluminum hydroxide gel. The rods were prepared as described in Example 1 with the following modifications. After filtration the PLGA/methylene chloride solution was not dried and reweighed. The addition of components and casting steps were done in a fume hood rather than under nitrogen. The swollen and redried aluminum hydroxide gel was prepared as follows.

A 1 mg/ml dried aluminum hydroxide gel suspension in phosphate buffered saline was prepared by stirring for 5 days at 37° C. in six Oak Ridge type centrifuge tubes. The tubes were centrifuged 25 minutes at 12,5000 rpm. The supernatants were removed and the pellets were then washed three times with freshly drawn Milli Q® water (Resistivity>18 M Ω•cm). After centrifugation, the pellets were vacuum dried for 6 days in a dessicator at room temperature and 0:1249 grams reswollen and dried gel was recovered.

Results of the swelling of aluminum hydroxide gel/PLGA rods prepared with either swollen and redried aluminum hydroxide gel as described above, or with dried aluminum hydroxide gel as purchased, are shown in FIG. 4.

Example 5

Preparation of a Formulation Containing Dried Aluminum Hydroxide Gel, PLGA and Dried Hepatitis A Vaccine A 1 ml aliquot of Hepatitis A Vaccine (HAV) containing about 22 μg/ml HAV antigen was extracted with 4 volumes of chloroform/methanol 2:1 (v/v) in a glass 15 ml centrifuge tube. The sample was vortexed vigorously after addition of solvent, then periodically (~30 minute intervals) for approximately 4 hours. Upper and lower phases were clarified by centrifugation at 600×g for 10 minutes. The upper phase, containing the HAV, was collected.

The extracted HAV sample was approximated to have a volume of 520 μl. It was added to a micro-concentrator unit with a 30,000 MW cutoff (Amicon #4208). The concentrator unit had been pre-rinsed by passing freshly drawn Milli-$Q^R$ water (Resistivity>18 M Ω•cm) through the unit. The assembled unit was centrifuged for a total of 90 minutes at 5,000 rpm in an SS•34 rotor in an RC-5B centrifuge. The concentrated HAV material was collected in a retentate cup provided with the unit and a steady, but very gentle stream of nitrogen was blown onto the liquid to dry the material. After ~30 minutes, a small amount of film-like material remained in the retentate cup. All of this material was used as described below.

A PLGA stock solution was prepared by addition of 100 ml HPLC grade $CH_2Cl_2$ to 10 grams 50:50 DL PLGA. The mixture was stirred overnight to dissolve the polymer. A considerable amount of fine gel-like particles remained undissolved. The liquid was filtered to remove this undissolved material. The liquid was pressure filtered through a prefilter backed by a 5 μm Teflon filter (Millipore Type LS). The weight of PLGA per volume of solution after filtration was determined to be 0.1005 g PLGA/ml filtrate.

Since it was desired to prepare ~1 gram of formulation that was 15% dried aluminum hydroxide gel, a total of 0.1486 grams dried aluminum hydroxide gel was added to the container of dried Hepatitis A Vaccine (HAV) described above, a small amount at a time. The dried aluminum hydroxide gel was stirred with a sterile syringe needle to abrade the dried film of HAV from the cup. The dried aluminum hydroxide gel/HAV mixture was added to a vial that contained 8.5 ml of stock PLGA solution (corresponding to ~850 mgs PLGA). After all dried aluminum hydroxide gel had been used to transfer as much of the HAV from the retentate cup as possible to the PLGA solution, the liquid was stirred rapidly to suspend the fine dried aluminum hydroxide gel particles and to try to break up the larger dried HAV film particles. After the suspension was stirred for ~20 minutes, the suspension was cast on a glass plate with a Boston-Bradley Blade (gap ~0.025 inches) and allowed to air dry for ~2½ hours when the homogeneous film was removed with a razor blade scraper and placed under vacuum to finish drying.

The vacuum dried casting (0.9517 g) was extruded into rods. The extrusion conditions were 62°–67° C. and ~5,000 lbs applied load. The resulting 0.43 grams of rod were flexible and opaque gray in color.

Example 6

In Vitro Release of Hepatitis A Virus From the Formulation Described in Example 5

To determine the release profiles of HAV from the formulation described in Example 5, segments of extruded rod were leached into buffer containing aluminum hydroxide gel. Rods were cut into segments of ~25 mm. Three segments were added to each of 3 microcentrifuge tubes. The gel containing buffer was prepared with a 1.3% suspension of Alhydrogel (diluted 1:20 in PBS with 0.1% $NaN_3$). (Alhydrogel was obtained from Superfos Biosector—a/s, Denmark, distributed by Sergeant Pulp and Chemical Co., Clifton, N.J., Cat. #2188-1). One ml of this suspension was added to each tube. The samples were placed in a 37° C. controlled temperature room. At intervals, the rod segments were transferred to new tubes and fresh aluminum hydroxide gel buffer as described above was added. After centrifugation, the pellets were collected and examined by ELISA for detection of HAV.

In a separate experiment, three samples of rods were cut into ~1 cm pieces and placed in vials containing PBS with 0.1% $NaN_3$ and held at 37° C. The dimensions were measured with a binocular microscope grid to monitor volume and surface changes. The rods were measured daily for 10 days and then twice a week thereafter. By Day 10, the rods had swollen to about 120% of initial size and some bubbles were observed on the sides of the rods. As time passed, these bubbles grew slightly until it was noticed on Day 22 that several of the bubbles appeared to have ruptured. Particulate matter could be seen in the vials. Some of the floating matter looked opaque. Other pieces looked like pieces of film, possibly from the ruptured bubbles. Between 4 and 5 weeks, substantial swelling occurred, a change from 120% of initial volume to ~170%. This disintegration and swelling coincided with release of HAV. The volume changes and HAV release for the formulation are illustrated in FIG. 5.

Example 7

Preparation of a Formulation Containing Dried Aluminum Hydroxide Gel, PLGA and Dried Inactivated Hepatitis A Vaccine Adsorbed to Aluminum Hydroxide Gel A batch of aluminum hydroxide gel adsorbed-HAV was prepared from inactivated and partially purified antigen. The aluminum hydroxide gel adsorbed-HAV was lyophilized. An aliquot of 83 µl of Alhydrogel solution was added to 2.5 ml of a solution containing 55 µg of HAV in a lyophilization flask fitted with magnetic stir bar. A variation of the lyophilization procedure described in European Patent #0130619 (date Mar. 15, 1989, application number 84107773.8) was carried out with aluminum hydroxide gel-HAV. After mixing for 30 minutes, a 500 µl aliquot was removed. NaCl, 34.1 mg, and 40.1 mg of lactose were added to the remaining solution and it was stirred continuously until these salts had dissolved. Another 500 µl aliquot was removed to a second lyophilizing flask. The contents of both flasks were shell frozen in liquid nitrogen and lyophilized. The flasks were removed from vacuum and stored in a desiccator until used.

A solution of 50:50 DL PLGA was prepared by stirring 10 g PLGA in $CH_2Cl_2$. The solution was passed through a series of stainless steel screens to remove gel particles, finally passing a 38 µm screen. This filtrate was pressure filtered, ~25 ml at a time, through a 1 µm retention glass, binder-free prefilter backed up by a 5 µm Teflon$^R$ filter. The filtrate was collected in a 500 ml Teflon$^R$ bottle. After removal of an aliquot for residual PLGA determination, the volume of filtrate was 120 ml and the concentration was 0.064 g PLGA/ml.

Sufficient dried aluminum hydroxide gel to comprise ~15% of formulation weight, 1.2353 g, was added to the lyophilization flask holding the larger portion of lyophilized aluminum hydroxide gel-HAV from above. The dried aluminum hydroxide gel was stirred to remove the lyophilized material from the flask walls. The combined materials were added to the PLGA filtrate. After stirring a few minutes, the suspension was cast onto 3 glass plates with a casting blade set at 0.025 inches. The glass plates were placed on racks in a drying chamber that had a steady stream of nitrogen passing through. After ~2 hours, the cast films were scraped from the glass plates and vacuum dried. The casting was extruded into rods. The rods were ground to a powder and the powder was sieved to obtain the fraction of 38–90 µm. 1.87 g was obtained.

Example 8

In Vitro Release of Hepatitis A Virus Absorbed to Aluminum Hydroxide Gel From the Formulation Described in Example 7

As described in Example 6, two types of in vitro studies (measurements of HAV release over time and rod swelling) were carried out with the formulation described in Example 7. Release studies were done on extruded rods cut into segments of ~25 mm. Three segments were weighed (~100 mg total) and transferred to each of three microcentrifuge tubes. An aluminum hydroxide gel containing buffer was prepared with Alhydrogel (1:20 dilution in PBS with 0.1% $NaN_3$) and was added to each of the samples. All samples were maintained at 37° C. At intervals, the samples are transferred to fresh Alhydrogel. The leachates were centrifuged and the pellets were assayed for HAV content by ELISA. This formulation showed HAV release beginning at Day 23. The initiation of rapid swelling was noted on Day 25. The volume changes and aluminum hydroxide gel adsorbed-HAV release profile for this formulation are shown in FIG. 6.

Example 9

In Vivo Activity of the Immunobooster Formulation Prepared as Described in Example 7

The in vivo test was designed to test both the ability of the immunobooster formulation to give a booster-like effect when given along with a primer dose of aluminum hydroxide gel-HAV and its ability to give a delayed release of the gel-bound HAV. The amount of primer dose given (0.15 ml) was that previously determined to give a positive result in a anti-HAV antibody ELISA test [seroconversion] in about half of a group of inoculated mice. The control groups in the study were: (1) vehicle control (aluminum hydroxide gel); (2) primer only; and (3) primer plus booster (a second dose of primer given at 4 weeks). The immunobooster dose (1×) contained approximately the same amount of HAV as that given in primer and booster doses (10–35 ng HAV/dose). The study groups were as follows: two groups received one primer dose injected simultaneously with the immunobooster at 1× or 5×, suspended in a carboxymethylcellulose solution, and one group received immunobooster alone, suspended in carboxymethylcellulose solution, at 5×. The test animals were CD-1 VAF male mice (28–34 g) from Charles River Laboratories. The Groups are summarized in Table 1.

The animals were bled from the orbital sinus at 4, 6, 8 and 10 weeks. The sera were analyzed neat and at various dilutions by an antibody HAV ELISA test which returns number of positive test results [seroconversions] per number of animals in the set at each dilution tested. The results are summarized by calculating the dilution at which each set of animals showed 50% seroconversion at each time point. The results are shown in graphical form in FIG. 7. It can be seen that while the immunoboosters alone have never given a significant amount of seroconversion, animals receiving the immunobooster along with a primer dose showed levels of anti-HAV equal to or higher than the levels seen in animals receiving primer plus traditional 4 week booster shots, and significantly higher than those receiving primer alone.

TABLE 1

IN VIVO TEST SCHEME

| Group | Aluminum Hydroxide Gel (ml) | Gel-HAV Primer (ml) | Immuno-booster (mg) | # of Animals |
|---|---|---|---|---|
| | Amounts Per Animal | | | |
| Controls | 0.15 | 0 | 0 | 3 |
| Primer Only | 0 | 0.15 | 0 | 5 |
| Primer + Booster (@ 4 weeks) | 0 | 0.15 | 0 | 5 |
| Immuno-booster 5X | 0 | 0 | 50 | 5 |
| Primer + Immuno-booster 1X | 0 | 0.15 | 10 | 10 |

TABLE 1-continued

IN VIVO TEST SCHEME
Amounts Per Animal

| Group | Aluminum Hydroxide Gel (ml) | Gel-HAV Primer (ml) | Immuno-booster (mg) | # of Animals |
| --- | --- | --- | --- | --- |
| Primer + Immuno-booster 5X | 0 | 0.15 | 50 | 7 |

Equivalents

Those skilled in the art will be able to ascertain, using no more than routine experimentation, many equivalents of the specific embodiments of the invention described herein.

These and all other equivalents are intended to be encompassed by the following claims.

We claim:

1. A method for preparing a polymer matrix including a swelling agent for bursting the matrix comprising, dissolving a hydrophic polymer in solvent, said hydrophobic polymer selected from the group consisting of poly(lactic/glycolic) acid copolymers (PLGA), polylactic acid (PLA), polyglycolic acid (PGA), polyesters, polyorthoesters, polylactones, polyanhydrides and polyaminoacids to form a polymer solution;

adding a swelling agent to said polymer solution, said swelling agent selected from the group consisting of aluminum hydroxide; aluminum phosphate; calcium phosphate; lanthanum, cerium, and cadmium salts; and bentonite to form a suspension, said swelling agent added in an amount sufficient to burst the matrix within a period of two weeks to one year when placed in an aqueous environment;

casting the suspension on a plate, to form a casting;

drying the casting under a vacuum to form a dried casting and, extruding the dried casting to form a shaped swelling agent/polymer matrix.

2. A method according to claim 1 wherein the adding and casting steps are conducted under nitrogen.

3. A method according to claim 1, further comprising adding an immunogen or adjuvant to the dissolved polymer prior to casting the suspension.

4. A method according to claim 1, further comprising adding an adjuvant that differs from the swelling agent to the dissolved polymer prior to casting the suspension.

5. The method according to claim 1 wherein the polymer matrix is extruded in the form of rods.

6. The method according to claim 1, further comprising grinding and sieving the extruded matrix to form a powder.

7. The method according to claim 1 wherein the polymer is poly(lactic/glycolide) acid.

8. The method according to claim 1 wherein the swelling agent is dried aluminum hydroxide gel.

9. The method according to claim 1 wherein the polymer is PLGA and the swelling agent is dried aluminum hydroxide gel, the dried aluminum hydroxide gel comprising between about 1% and about 40% of the matrix.

10. A method as claimed in claim 1 further comprising, adsorbing an immunogen on the swelling agent to form a complex prior to adding the swelling agent to form the suspension.

11. The method according to claim 1 further comprising, adsorbing an immunogen on the swelling agent to form a complex, drying the complex, and then adding the complex to form the suspension.

12. A method of immunizing a subject comprising the steps of:

administering an immunogen/hydrophobic polymer matrix to a subject, said immunogen/hydrophobic polymer matrix comprising a hydrophobic polymer, immunogen and a swelling agent, said hydrophobic polymer capable of biodegradation in vivo and selected from the group of polymers consisting of poly(lactic/glycolic) acid copolymers (PLGA), polylactic acid (PLA), polyglycolic acid (PGA), polyesters, polyorthoesters, polylactones, polyanhydrides and polyaminoacids, said swelling agent selected from the group consisting of aluminum hydroxide; aluminum phosphate; calcium phosphate; lanthanum, cerium, and cadmium salts; and bentonite; said immunogen present in an effective amount to elicit an immune response in a subject; said swelling agent absorbing water from the subject and expanding said matrix as said polymer is degraded, to release said immunogen in a burst after a period of 2 weeks to 12 months.

13. The method of claim 12 wherein said matrix comprises an adjuvant.

14. The method of claim 13 wherein said adjuvant is released with said immunogen.

15. The method of claim 13 wherein said adjuvant and said swelling agent is aluminum hydroxide gel from which aluminum hydroxide is released with immunogen.

16. The method of claim 12 wherein said swelling agent is dried-aluminum hydroxide gel comprising between about 1% and about 40% of the matrix.

17. The method of claim 16 wherein said aluminum hydroxide gel comprises between about 5% and about 20% of the matrix.

18. The method of claim 17 wherein said aluminum hydroxide gel comprises about 10% and about 15% of the matrix.

19. The method of claim 12 wherein said polymer is PLGA having a composition of 50:50 D, L lactide/glycolide.

20. The method of claim 12 wherein said immunogen and swelling agent are present in the matrix as a complex.

21. The method of claim 12 wherein said immunogen is released primarily in a period beginning 21 days to 6 months after administration.

22. The method of claim 12 further comprises the step of administering free immunogen to said subject.

23. The method of claim 22 wherein said free immunogen is administered with the immunogen/hydrophobic polymer matrix.

24. The method of claim 12 wherein said polymer matrix is administered as a suspended powder, or as suspended beads, or as a rod.

25. A kit for delivering immunogen to a subject comprising a package containing:

a) one or more vessels containing an immunogen/hydrophobic polymer matrix, said immunogen/hydrophobic polymer matrix comprising an immunogen, swelling agent, and a hydrophobic polymer, said hydrophobic polymer capable of biodegradation in vivo and selected from the group of polymers consisting of poly(lactic/glycolic) acid copolymers (PLGA), polylactic acid (PLA), polyglycolic acid (PGA), polyesters, polyorthoesters, polylactones, polyanhydrides and polyaminoacids to form a polymer solution, said swelling agent suspended in said polymer in an amount sufficient to burst said matrix, said swelling agent consisting of aluminum hydroxide; aluminum phosphate; calcium phosphate; lanthanum, cerium, and cadmium salts; and bentonite; said immunogen present in an effective amount to elicit an immune response in a subject; said swelling agent for absorbing water from the subject and expanding said matrix as said polymer is degraded, to release said immunogen in a burst after a period of 3 weeks to 12 months.

26. The kit of claim 25 further comprising a syringe for administering said immunogen/hydrophobic polymer matrix.

27. A method of immunizing a subject comprising the steps of:

administering an immunogen/hydrophobic polymer matrix to a subject, said immunogen/hydrophobic polymer matrix comprising a hydrophobic polymer, immunogen and a swelling agent, and having an initial volume, said hydrophobic polymer capable of biodegradation in vivo and selected from the group of polymers consisting of poly(lactic/glycolic) acid copolymers (PLGA), polylactic acid (PLA), polyglycolic acid (PGA), polyesters, polyorthoesters, polylactones, polyanhydrides and polyaminoacids; said swelling agent selected from the group consisting of aluminum hydroxide; aluminum phosphate; calcium phosphate; lanthanum, cerium, and cadmium salts; and bentonite; said immunogen present in an effective amount to elicit an immune response in a subject; said swelling agent present in amounts comprising 1% to about 40% of said matrix for absorbing water from the subject and expanding said matrix as said polymer is degraded, said matrix containing an effective amount of said immunogen for a period of 2 weeks to 12 months, until said swelling agent expands said matrix to a volume greater than one hundred twenty percent of the initial volume, and releases an effective amount of immunogen to create an immune response.

28. A method of immunizing a subject comprising:

administering a free immunogen to the subject to stimulate a primary immune response; and, administering an immunobooster to the subject, wherein the immunobooster includes an immunogen, a hydrophobic polymer matrix and a swelling agent, wherein the hydrophobic polymer matrix and the swelling agent are present in an amount sufficient to burst in a period of between 2 weeks and 1 year in an aqueous environment causing a pulse release of the immunogen to stimulate a secondary immune response in the subject.

29. The method of claim 28, wherein the swelling agent is a dried-aluminum hydroxide gel.

30. The method of claim 28, wherein the swelling agent comprises from approximately 5% to approximately 20% of the hydrophobic polymer matrix.

31. The method of claim 28, wherein the swelling agent comprises from approximately 10% to approximately 15% of the hydrophobic polymer matrix.

32. The method of claim 28, wherein the period of time to stimulate a secondary immune response is from two weeks to twelve months.

33. The method of claim 28, wherein the period of time to stimulate a secondary immune response is from twenty-one days to six months.

34. The method of claim 28, wherein the immunobooster is administered as a solid dose.

35. The method of claim 28, wherein the polymer is Poly(lactic/glycolic) acid having a composition of 50:50 D,L lactic/glycolic.

36. A method of immunizing a subject comprising administering an immunobooster to the subject, wherein the immunobooster includes an immunogen, a hydrophobic polymer matrix, and a swelling agent, wherein the hydrophobic polymer matrix and the swelling agent are present in an amount sufficient to burst in a period of between 2 weeks and 1 year in an aqueous environment causing a pulse release of the immunogen to stimulate a secondary immune response in the subject.

37. The method of claim 36, wherein the swelling agent is dried-aluminum hydroxide gel.

38. The method of claim 36, wherein the swelling agent comprises from approximately 5% to approximately 20% of the hydrophobic polymer matrix.

39. The method of claim 36, wherein the swelling agent comprises from approximately 10% to approximately 15% of the hydrophobic polymer matrix.

40. The method of claim 36, wherein the period of time to stimulate a secondary immune response is from two weeks to twelve months.

41. The method of claim 36, wherein the period of time to stimulate a secondary immune response is from twenty-one days to six months.

42. The method of claim 36, wherein the immunobooster is administered as a solid dose.

43. The method of claim 36, wherein the polymer is Poly(lactic/glycolic) acid having a composition of 50:50 D,L lactic/glycolic.

44. The method of claim 36, further comprising the step of administering free immunogen to the subject to stimulate a primary immune response.

45. The method of claim 44, wherein the free immunogen is administered independently of the immunobooster, such that the free immunogen is present in a first formulation, and the immunobooster is present in a second formulation.

46. The method of claim 44, wherein the free immunogen is administered with the immunobooster in a single formulation.

47. A kit for delivering immunogen to a subject comprising: a package containing:

packaged initial immunogen, wherein the initial immunogen is in an amount effective for stimulating a primary immune response, packaged immunobooster, wherein the immunobooster includes an immunobooster immunogen, a hydrophobic polymer matrix and a swelling agent, and wherein the hydrophobic polymer matrix and the swelling agent are present in an amount sufficient to burst in a period of between 2 weeks and 1 year in an aqueous environment causing a pulse release of the immunobooster immunogen to stimulate a secondary immune response, and instructions providing information to the user regarding the use of the immunobooster for delivering immunogen to a subject to stimulate a secondary immune response.

48. The kit of claim 47, further comprising a syringe.

* * * * *